United States Patent [19]

Förster

[11] Patent Number: 5,638,000

[45] Date of Patent: Jun. 10, 1997

[54] METHOD AND APPARATUS FOR ELECTRO-MAGNETICALLY TESTING ELONGATED OBJECTS

[75] Inventor: Friedrich M. Förster, Pfullingen, Germany

[73] Assignee: Institut Dr. Friedrich Forster, Reutingen, Germany

[21] Appl. No.: 279,499

[22] Filed: Jul. 22, 1994

[30] Foreign Application Priority Data

Aug. 26, 1993 [DE] Germany ................. 43 28 712.3

[51] Int. Cl.⁶ ........................................... G01N 27/90
[52] U.S. Cl. ............................................... 324/238
[58] Field of Search ............................. 324/232–243, 324/227, 228, 262, 219–221

[56] References Cited

U.S. PATENT DOCUMENTS

| | | | |
|---|---|---|---|
| 3,146,395 | 8/1964 | Quittner | 324/241 |
| 3,500,181 | 3/1970 | Jackson | 324/238 |
| 3,518,533 | 6/1970 | Arnelo | 324/238 |
| 3,731,184 | 5/1973 | Goldberg et al. | |
| 3,936,733 | 2/1976 | Clary | 324/262 |
| 3,940,690 | 2/1976 | Suhr et al. | 324/242 |
| 4,351,184 | 9/1982 | Garner et al. | 324/238 X |
| 4,480,225 | 10/1984 | Nance et al. | 324/238 |
| 4,507,610 | 3/1985 | Nakaoka | 324/238 |
| 4,659,990 | 4/1987 | Torre | 324/238 |
| 4,719,422 | 1/1988 | de Walle et al. | 324/238 |
| 4,829,247 | 5/1989 | Wallrafen | 324/207.25 |
| 4,893,077 | 1/1990 | Auchterlonie | 324/233 X |
| 4,906,927 | 3/1990 | Urata et al. | 324/238 |
| 5,041,786 | 8/1991 | Takaishi et al. | 324/238 X |
| 5,412,319 | 5/1995 | Ciani | |

FOREIGN PATENT DOCUMENTS

| | | | |
|---|---|---|---|
| 0066521 | 8/1982 | European Pat. Off. | |
| 3527972 | 2/1987 | Germany | |
| 3802072 | 9/1988 | Germany | |
| 59-200956 | 11/1984 | Japan | |
| 63-11853 | 1/1988 | Japan | |
| 63-271157 | 11/1988 | Japan | |
| 63-274859 | 11/1988 | Japan | 324/220 |

*Primary Examiner*—Sandra L. O'Shea
*Assistant Examiner*—Roger Phillips
*Attorney, Agent, or Firm*—Bell, Seltzer, Park & Gibson, P.A.

[57] ABSTRACT

A method and apparatus for electro-magnetically testing surface regions of elongated test objects for irregularities, such as flaws, and which is particularly suitable for testing test objects with non-circular or elliptical cross sections. Testing is performed by at least one coil, particularly an eddy current coil, through which a test object passes. The test coil has a coil plane passage of predetermined cross-section, and a modification of the passage cross-section of the test coil can be obtained by tilting the test coil. The test coil can optionally be rotated about an axis defined by the travel direction of the test object, and may also be moved in directions perpendicular to the travel direction. A disclosed apparatus for performing the method has several tiltable and rotatable and/or slidable test coils which are successfully arranged in the travel direction in the form of a coil group.

21 Claims, 3 Drawing Sheets

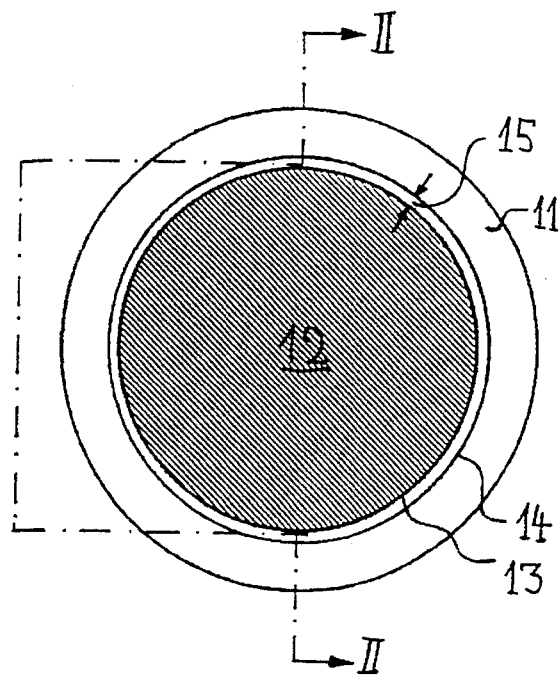
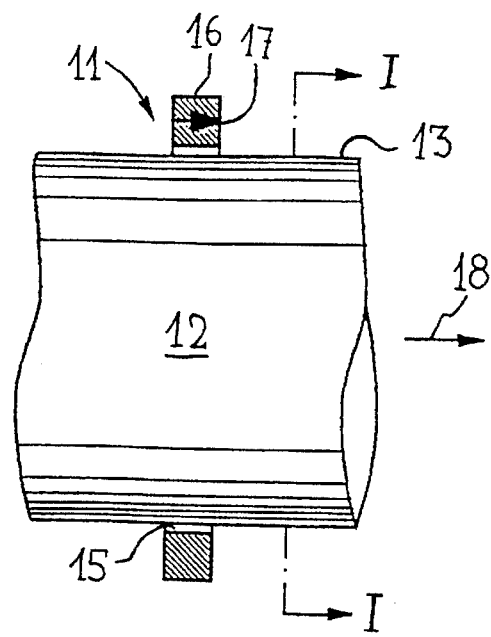
Fig. 1              Fig. 2
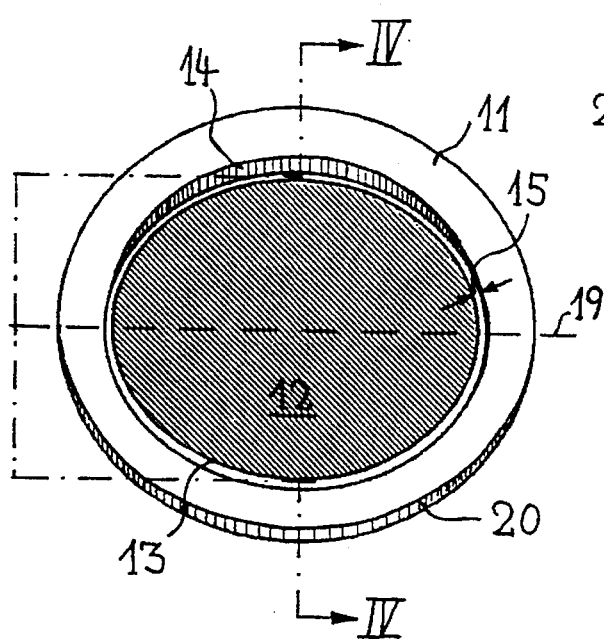
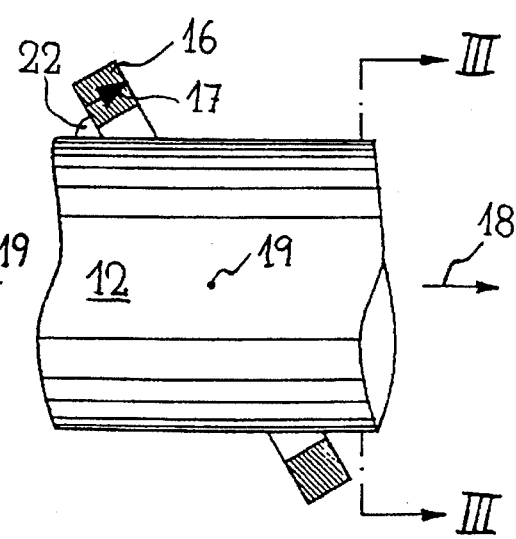
Fig. 3              Fig. 4

METHOD AND APPARATUS FOR ELECTRO-MAGNETICALLY TESTING ELONGATED OBJECTS

BACKGROUND OF THE INVENTION

The invention relates to a method for testing elongated objects, optionally having a non-circular cross-section by means of at least one test coil through which passes a test object and having a predetermined coil plane passage cross-section, in particular an eddy current coil, as well as to a testing apparatus for performing the said method with at least one test coil having a predetermined coil plane passage cross-section and optionally a reception member for receiving the test coil. The invention more particularly relates to the problem of non-destructively and substantially uninterruptedly testing for surface defects metallic semifinished products having a non-circular cross-section.

PRIOR ART

Testing for surface defects within the framework of a quality control on metallic semifinished products such as wires, rods or tubes are at present frequently performed on the basis of eddy current technology. A known apparatus of this type for testing test objects having a circular cross-section has a test coil with a circular coil plane passage cross-section, which can be brought into the production line of a semifinished product in such a way that the test object passes through the test coil. The test coil subject to the action of high frequency a.c. voltage induces high frequency eddy currents, whose induced magnetic fields are received again by the test coil as a measuring signal. Surface defects on the part of the test objects give rise to interference in the eddy currents and therefore to changes in the measuring signal. The test signal is generally obtained from the comparison of adjacent test material cross-sections. For receiving a significant measuring signal, the test coil should be relatively close to the surface to be tested.

SUMMARY OF THE INVENTION

An object of the invention is to provide a method making it possible to also test elongated objects having a non-circular cross-section with preferably easily manufacturable test coils having test coil passage cross-sections of simple form, as well as an apparatus for performing such a test. The apparatus must in particular be adaptable to test objects having different cross-sectional shapes.

According to the invention at least one test coil, particularly an eddy current coil, is so positioned relative to a test object passing through that, considered in the object travel direction, its test cross-section can differ from the cross-sectional shape in the case of a plan view of the test coil, here referred to as the coil plane passage cross-section. If the test cross-section of the test coil is adapted to the shape of the cross-section of the object to be tested in such a way that the distance between the object and the test coil along the entire circumference of the object is small and roughly the same, then the interaction between the test coil and the test object along the entire circumference of the latter is substantially identical. Independently of their position on the circumference of the test object, similar defects then lead to similar measuring signals, which can lead to particularly easily interpretable results of the material testing.

Test coils according to the invention are not restricted with respect to the coil plane passage cross-section to a circular shape. It is also conceivable to use coils having a substantially rectangular cross-section, optionally with rounded corners, or also those having more complex shapes of the coil plane passage cross-section. However, preference is given to circular test coils for manufacturing reasons and because they are relatively simple to calculate.

Particularly for the testing of test objects having an elliptical cross-section, an embodiment is particularly advantageous in which the test coil is circular and the coil plane is set by an angle differing from 90° with respect to the test object travel direction. In the case of an elliptical test cross-section of the test coil produced by a setting angle differing from 90° the ratio of the diameter of the ellipse is substantially determined by the size of the setting angle. This more particularly applies if the untilted test coil is short in the travel direction.

For testing test parts with different radius ratios it is advantageous to position the coil plane tiltably with respect to the test object travel direction. This is achieved by providing tilting means for the test coil. This could be brought about in that a conventional testing apparatus with the test coil is made tiltable as a whole, e.g. by using adjustable feet. Advantageously this can also take place by mounting the test coil within or on a reception member of the testing apparatus, the test coil being rotatable about an axis, which is here referred to as the tilt axis. The tilt axis can be tangential to the test coil internal diameter or to a mounting support of the test coil, or can be parallel to a secant or to a diameter of the test coil. When the tilt axis is parallel to the diameter it is advantageous for the centre of the test coil not to change its position with respect to the reception member of the apparatus or the object guided by the test coil during tilting.

A tilting of a test coil about she tilt axis can e.g. be brought about in that in the vicinity of the circumference of the test coil or a mounting support surrounding the test coil on the reception side are provided one or more bearings, in which are rotatably mounted parts, e.g. shafts fixed to the test coil. It is also possible on the reception side for fixed parts, such as shafts, to engage in bearings located on the test coil or on a corresponding mounting support. The locations of the bearings and the orientation of the rotation axis of the rotation which is possible in the bearings is fixed by the path of the tilt axis. For the bearing of a test coil it is only necessary to have a single bearing, which can be positioned on or within a reception member of the testing apparatus. However, the test coil bearing is made particularly stable by bearings positioned in diametrically facing manner at two points of the test coil circumference and as a result of which the coil can be made tiltable about its diameter.

It would be conceivable to have bearings, e.g. ball or roller bearings, directly on the reception member of the testing apparatus. This would lead in simple manner to tiltable coils. In the interest of high variability of the testing apparatus the bearings can also be located on a movable rotary member at least partly surrounding the test coil or on a sliding member. Engagement need not directly take place on the reception member or the rotary member or the sliding member. It is also possible to provide bearing holding means between the test coil and the member on which the test coil is mounted, referred to as bearing member for short. This can be advantageous more particularly when interchanging test coils of different diameters, e.g. when adapting the apparatus to test objects having different cross-sectional dimensions and/or shapes. It would then merely be necessary to fix the bearing holding means, which are appropriately associated with the test coil, on the bearing member, e.g. in rigid manner by a screw connection, but preferably also in movable manner. Therefore the bearing holding means could be movably mounted with respect to the bearing member in guides and preferably linearly in a direction parallel to the travel direction.

The electrical connection of the test coil over and beyond the bearing from the area of the coil to the area of the bearing member or optionally the bearing holding means and optionally from there to a bearing member can be brought about by standard electrical connecting means, e.g. by wires or sliding contacts. A connecting means associated with a test coil is preferably located where the relative movement between the coil and the bearing member or the bearing holding means is relatively small, i.e. preferably in the vicinity of the bearings.

In the case of test coils, whose measuring principle is based on generating and/or using in particular high frequency electrical a.c. voltages, i.e. particularly in the case of eddy current coils, it can be advantageous to produce the electrical connection of the coils via transmitters acting in transformer manner. In the case of these transmitters, where there is no need for a contact between the transmitter parts associated with the test coil and those associated with a bearing member or bearing holding means, in that between a transformer-type transmitter of the test coil and preferably such a transmitter on the bearing member or bearing holding means an air gap can be left, the risk of contact wear and/or contact deterioration by corrosion or the like would not exist and the relevant maintenance work would be obviated. The electrical transmission can also take place in such a way that the bearing shafts fulful the function of a transformer core and in each case on the test coil side and on the side e.g. of the bearing holding plates the bearing shaft is surrounded by transmitting or receiving windings.

As a result of the tiltability of a test coil in a testing apparatus it is possible to achieve that e.g. with a circular test coil it is possible to test both circular test objects and those having elliptical cross-sections with different radius ratios. If the test coils of a testing apparatus can be easily interchanged with those having different cross-sectional dimensions and optionally different cross-sectional shapes, then it is possible to advantageously test with a single testing apparatus test objects having the most varied cross-sectional dimensions.

The advantages of tiltable test coils could also be utilized for test objects having a non-elliptical cross-section and in particular for those whose cross-sectional circumference can be formed by circular or elliptical segments. Thus, oval cross-sections could be formed by a circular segment and an elliptical segment. In the same way, by two test coils having an elliptical test cross-section turned with respect to one another by 90° about the travel direction a substantially cross-sectionally rectangular, four-surface test object could be covered. It would also be possible to test test objects with a lenticular cross-section if two elliptical test cross-sections with an identical or different radius ratio are staggered e.g. in the direction of the short radius of the ellipses. Three elliptical passage cross-sections rotated by 120° about an axis parallel to the travel direction could produce a hexagonal, common test cross-section. If the rotation axes of the 120° rotations do not coincide, then cross-sectionally triangular test objects could be covered by the test coils in such a way that each face of the object is positioned close to an elliptical segment of a test coil.

Such tests of parts of the surface of a test object by test coils tilted under certain circumstances could be achieved in that several testing apparatuses according to the invention are successively arranged in the object travel direction. Considered in the travel direction, they could be staggered and could also be turned relative to one another about axes parallel to the travel direction. Inter alia for reasons of the constancy of the measuring conditions and the effort in evaluating the measuring signals and also for cost reasons, it could be particularly advantageous to provide possibilities for rotating and/or sliding tilted and/or untilted test coils within an apparatus. For this purpose the bearing member, in which a test coil is tiltably mounted, could be constructed in such a way that it is rotatable about a rotation axis parallel to the travel direction. The bearing member is then a rotary member. Appropriately this can e.g. also be achieved in that the rotary member is constructed in a substantially sleeve-like manner with a substantially circular outer circumference and along areas of its circumference it is mounted in a further member, e.g. by ball or roller bearings. Between the rotary member and said further member the electrical connection can be provided by wires, sliding contacts or transformer-type transmitters.

Appropriately the member in which the rotary member is mounted is displaceable in at least one direction perpendicular to the travel direction, so that the member is a sliding member. The sliding of the sliding member can take place along suitable guide means, e.g. by means of guide rails or also along dove-tail connections. The guide means could also be positioned in such a way that their sliding directions, considered in the travel direction, stand vertically on one another. In such an apparatus a tiltable test coil can be positioned in random manner relative to the test object.

Although for testing purposes a single coil can be adequate, in order to attain better test results frequently use is now made of special arrangements of several coils with a suitable electric wiring between them. Thus, a single coil or a number of series-connected coils responds both to abrupt and to continuous changes of material characteristics of the traversing test material. Thus, it is possible to detect both short and long defects. The measuring signals are generally easy to evaluate and indicate the overall length of surface damage. In the case of so-called absolute coils there is a tendency to drift in the case of temperature instability and they are also sensitive to guidance inaccuracies on the part of the test object. However, if at least two following test coils are connected against one another, a differential connection is produced. Test coils in differential connection are not sensitive to gradual changes to material characteristics or dimensions and do not have a drift tendency during temperature instability. They are also less susceptible to guidance inaccuracies than absolute test coils. The insensitivity to gradual changes of the test material can, however, lead to continuous defects not being detected. Only the start and finish of an extensive defect are detected and the signals to be evaluated can be very complicated. It is therefore advantageous to provide in a testing apparatus a combination of absolute test coils and those in a differential connection with respect to one another.

The advantages of such connections can be utilized in the testing apparatus in that several successively arranged test coils in the travel direction form a coil group. Preferably the test coils of a coil group are mounted on a common bearing member, e.g. on the reception member or on the rotary member. If the tilt axes of the test coils of a test group are arranged parallel to one another in a plane containing the travel direction, then several similarly tilted, successively arranged test coils appear as a single coil in the travel direction.

Within the coil group by suitable wiring of the outputs of the coils, it is possible to connect test coils both as absolute coils and as differential coils, but preferably as a combination of both absolute and differential coils. Thus, it is possible to utilize the specific advantages of each of the two connection types in a measuring process.

The individual test coils of a coil group could be arranged in spaced succession. In the interest of a good uniformity of the electromagnetic field within the coil group it is, however, appropriate to arrange the test coils of a coil group in directly adjacent succeeding manner, the individual test coils preferably being very short in a direction perpendicular to the coil plane. The inner surface of a coil group of tilted test coils appears to be stepped further removed from the areas of the bearings, the height of the inclined steps decreasing with decreasing length of the individual test coils and decreasing tilt from the plane perpendicular to the travel direction. Within the coil group it is possible to produce a very uniform electromagnetic a.c. field, which is advantageous for the simple evaluation of the measuring signals. If within a testing apparatus are successively arranged several such coil groups, which are optionally independently tiltable and/or rotatable and/or slidable, then with a testing apparatus of this type it is possible to produce the aforementioned, different passage projections for test objects. When testing for surface defects with respect to each surface only those coil segments make a significant contribution to the measurement past which the test object surface is moved with a relatively limited spacing. The size of this spacing is correlated with the range of the electromagnetic a.c. fields produced by the eddy currents.

The setting of a desired passage projection of the testing apparatus can take place by manually or automatically operable setting means. It is conceivable to use e.g. detachable and refixable slides or the like, which in each case act on the movably mounted members. However, preference is given to settings by means of screwable setting means, i.e. setscrews or threaded spindles acting on the individually movable parts. Thus, a tilt setting means for setting the tilting state of a test coil or coil group with its screwing direction parallel to the object travel direction can engage on at least one of the coils and reduce or increase the setting angle when screwing in or unscrewing. Similarly constructed threaded spindles or setscrews could act in the direction parallel to the guide members on the sliding members and slide same during rotation. Rotatably mounted bearing members could be manually adjusted in the rotation state and fixed by simple fixing means such as e.g. fixing screws. The adjustment of the setting means can take place manually. Particularly in the case of uses, where frequent test cross-section changes must take place, all the setting means can be automated in simple manner, e.g. by installing regulatable stepping motors.

It is advantageous for the present setting of each of the settable members to be visible from outside the testing apparatus. In a simple case this can be achieved by markings on the particular members, whose relative position provides the user with the information concerning the setting of the testing apparatus. It is also possible to use optoelectronic indicating means, i.e. displays of the most varied types, supplied with setting information e.g. by means of inductive displacement transducers, can be used for displaying the setting state of the testing apparatus. A particular combination of the individual set values of the movably mounted members of the testing apparatus corresponds to each test cross-section.

The term test coil can also cover all devices which are used for recording or producing and recording spatial distributions of physical measured quantities and which can be brought into a spatial relationship with the test object, e.g. also coils for measurements based on the magnetic stray flux principle.

These and further features and constructions of the invention can be gathered from the claims, description and drawings, the individual features being realizable singly or in the form of subcombinations in an embodiment of the invention and in other fields and can represent advantageous, independently protectable constructions for which protection is hereby claimed.

Embodiments of the invention are described hereinafter relative to the drawings.

BRIEF DESCRIPTION OF THE DRAWINGS

FIG. 1 is a diagrammatic view of a test coil in the travel direction of a sectionally represented test object.

FIG. 2 is a side view of the test coil shown in FIG. 1 in section with a test object guided by the coil.

FIG. 3 is a diagrammatic view of a tilted test coil in the travel direction of a sectionally represented test object having an elliptical cross-section.

FIG. 4 is a diagrammatic side view of the tilted test coil shown in FIG. 3 in section with a test object guided by the coil.

DESCRIPTION OF AN EMBODIMENT

Figure 5:
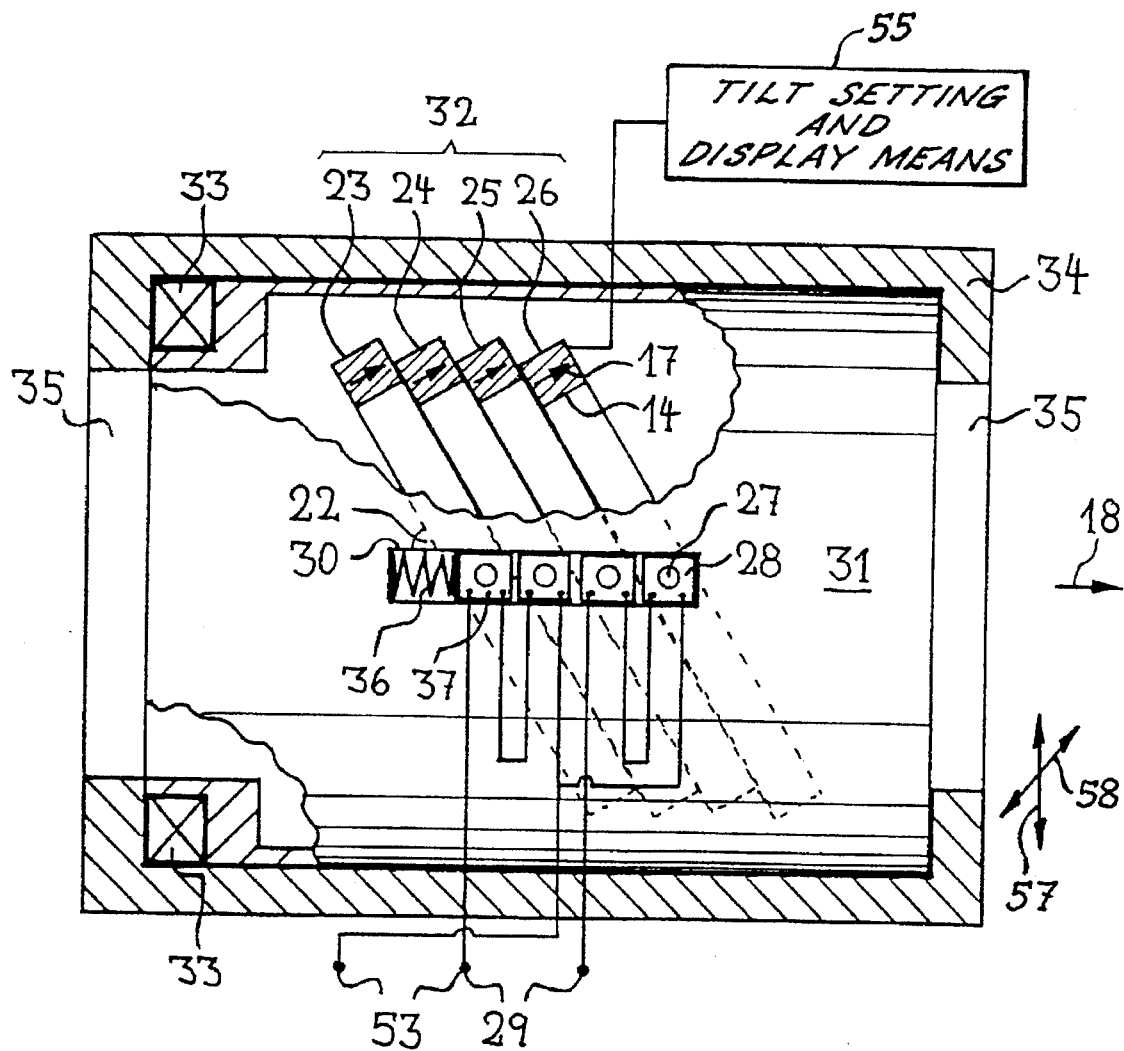
FIG. 5 is a diagrammatic side view in part section of a testing apparatus with a coil group formed from tilted test coils.

FIG. 1 shows a test coil 11 with a circular coil plane passage cross-section. A test object 12 with a circular cross-sectional surface is passed in a direction perpendicular to the paper plane through the test coil 11. A small test spacing 15 exists between the test object surface 13 and the inner area 14 of the test coil facing it. If the test coil 11 is supplied with a high frequency a.c. current then in the vicinity of the test object 12 a high frequency magnetic a.c. field is generated, which induces electric eddy currents in the test object and the intensity thereof decreases towards the object centre. The eddy currents close to the surface in turn induce magnetic a.c. fields, which interact over and beyond the test spacing 15 with the test coil 11. In the case of eddy current probes a crack close to the surface, i.e. an area where the material is missing close to the surface, by disturbing the eddy currents close to the surface. The change in the magnetic fields induced by the eddy currents in the vicinity of the crack is detected by the test coil and used for the identification of defects. Measurement takes place in contactless and non-destructive manner.

The side view of FIG. 2 shows the test coil 11 in section, it being possible to see the winding 16 and its winding direction is indicated by the arrows 17. The test object 12 is guided in the travel direction 18 through the test coil 11.

FIG. 3 shows the same test coil as in FIG. 4, but with the difference that the coil 11 in FIG. 3 is so tilted around the tilt axis 19 using tilting means that in the upper region of the test coil its inner area 14 is visible. Thus, this area is tilted rearwards out of the paper plane, whilst the coil outer circumference 20 can be seen in the diametrically opposite area of the test coil. A test object 12 with an elliptical cross-section is passed through the tilted test coil 11 perpendicular to the paper plane and almost completely fills the substantially elliptical test cross-section of the tilted test coil. There is only a small test spacing 15 in the region of the test object surface between the object and the coil. The side view of FIG. 4 belongs to the view shown in FIG. 3 and illustrates that the test coil 11 has been counterclockwise tilted about the tilt axis 19. The setting angle 22 between the test coil plane and the travel direction 18 diverges from 90° in the case of a tilted coil.

In FIG. 5 four similar test coils 23, 24, 25, 26 are arranged in succession in the travel direction 18 tilted by the same setting angle 22 against said direction 18. The arrows 17 indicate that all the coils have the same winding direction. Each of the four coils has diametrically facing bearing shafts 27, whereof in each case the faces facing the viewer are shown in the drawing. The bearing shaft 27 fixed to the coils engage in ball bearings, which are not shown in the drawing. These ball bearings are located in bearing holding means, which in the represented example are constructed in the form of bearing holding plates 28 having a rectangular cross-section. In the vicinity of the bearing shafts 27 the test coils 23, 24, 25, 26 are electrically connected to the area of the bearing holding plates 28.

The electrical connection to the outside from the area of the bearing holding plates 28 is symbolically indicated in FIG. 5 by line symbols. It can be seen that the coil 23 is connected in series with the coil 24 and that the coil 25 is connected in series with the coil 26. The two in each case series-connected coil pairs 23, 24 or 25, 26 are connected against one another and their overall signal in the form of a differential signal is applied to the output terminals 29. It would obviously also be possible to have taps between the test coils. Thus, e.g. at the output terminals 53 could be tapped an absolute signal produced in the coils 23, 24.

The four bearing holding plates 28 successively arranged in the travel direction 18 are slidably guided in the latter in a guide recess 30. The guide recess 30 is constructed in the rotary member 31, which considered in the travel direction 18 has a circular outer circumference and its area surrounding the coil group 32 is constructed in the manner of a tube. The rotary member 31 is mounted by means of bearings 33 in such a way that it can be rotated about its central axis parallel to the travel direction 18. By means of the bearings 33 the rotary member 31 is rotatably mounted in the sliding member 34. The latter, which is only diagrammatically shown in FIG. 5, can be moved in known manner, e.g. by dove-tail guides or the like in two different directions as illustrated schematically by arrows 57, 58 standing perpendicular on one another and on the travel direction 18. The sliding member 34 has passages 35 through which a test object can be guided in the vicinity of the bearing member 31 and the test coil group 32.

FUNCTION

In the case of the apparatus of FIG. 5 the test coils can obviously also be set perpendicular to the travel direction 18, so that the setting angle 22 is 90°. Considered in the travel direction 18, the apparatus then has a cross-section as shown in FIG. 1. The individual coils of the coil group 32 are immediately adjacent to one another. In this tilting state the bearing holding plates 28 are roughly in engagement with their unguided lateral faces. The engagement of the individual test coils is ensured by means of compression springs 36, which engage on the outer bearing holding plate 37 facing the same. In this position it is possible to test test objects having a circular cross-section and a corresponding size.

If when using the apparatus it is necessary to test a test object having a cross-section such as corresponds to the test object 12 in FIG. 3, then a setscrew tilt setting and display means 55 including a setscrew is actuated for the tilting state of the coils of the coil group 32 and engages in a direction parallel to the travel direction 18 on the coil 26 above the guide recess 30. On inserting the setscrew the setting angle 22 decreases and the short radius of the elliptical test cross-section of the test coil group is reduced. The setting angle 22, which is necessary for a specific radius ratio of an elliptical test cross-section, can be derived from simple geometrical relations. Importance is hereby attached to the length of a single, untilted test coil in the travel direction. It is preferably chosen in such a way that in the case of the tilted test coil the spacing between the inner area 14 thereof and the test object essentially only changes so little that both the parts of the inner area 14 extending nearest to the test object and also the parts furthest therefrom still effectively contribute to testing. The test coils are consequently preferably short coils.

The force exerted by the setscrew on the test coil 26 and which leads to a tilting movement of the latter, is transferred by it by force closure to its adjacent coil 25 and by force closure to all the other coils of the group. With increasing tilting, i.e. decreasing setting angle 22, the bearing holding plates 28 are moved away from one another counter to the tension of the compression spring 36, which ensures that the force closure between the individual coils of the group is maintained. For example, by not shown restoring springs it is possible to ensure that the force closure is also maintained if the set-screw is moved in the other direction, the setting angle 22 again increasing and the bearing holding plates 28 moving closer together. On setting the desired test cross-section of the coil group, then a test object can be guided by the apparatus and the test can commence. The setting of the test cross-section can also take place by the test object guided by the testing apparatus or an object having the same cross-section, whereby then the coil group can be tilted to such an extent that the upper or lower inner areas 14 of the test coils contact the test object or object. By turning back the set-screw the contact can then be removed and the test can commence.

FIGS. 6a–6e diagrammatically show certain of the possible test cross-section variants, which can be obtained by a combination of optionally tilted, optionally also turned against one another and optionally also displaced against one another test coils or coil groups. There can be several subassemblies, as shown in FIG. 5, which are successively arranged in the travel direction within a testing apparatus. It would also be conceivable to provide several simply constructed testing apparatuses based on the principle of FIG. 5, where no sliding element is provided, but where a casing is used in place thereof. Then, several such cases could be optionally successively staggered.

Figure 6A:
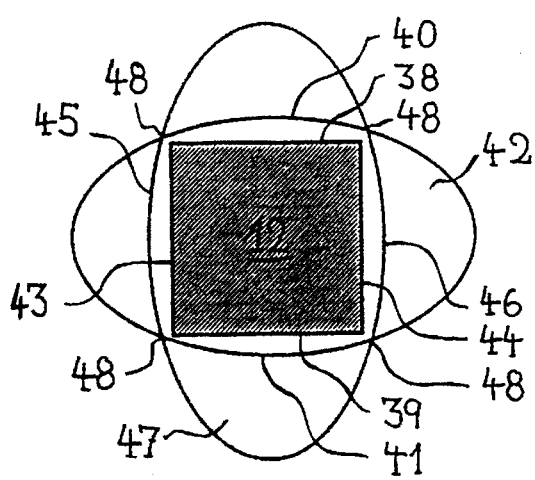
FIGS. 6a–6e are diagrammatic representations of different test cross-sections realizable by the testing apparatus.

The ellipses or circles in FIGS. 6a–6e symbolize the inner boundaries of test cross-sections of untilted or tilted coils or coil groups successively arranged in the travel direction. In FIG. 6a there are two coils or coil groups having the same diameter and same setting angle turned by 90° with respect to one another about the travel direction of the test object 12, the travel direction being perpendicular to the paper plane in FIGS. 6a–6e. The test object 12 has a square cross-sectional surface, the facing lateral faces 38, 39 of elliptical segments 40, 41 of the test coil 42 being tested. The same applies for the facing lateral faces 43, 44, which are tested by the elliptical segments 45, 46 of the test coil 47.

Essentially the test coils are only so close to the surfaces of the test object 12 between the overlap areas 48 that significant eddy current signals can be received there. The different sensitivity of the methods between the individual overlap areas 48, which is caused by the fact that the spacing between the test surface and coil segment changes along the segment, is of minor importance in many applications, particularly if it is borne in mind that the test information from which it can be derived whether or not there is a defect, is obtained from the comparison of the integral signals of following test part cross-sections in the travel direction.

Figure 6B:
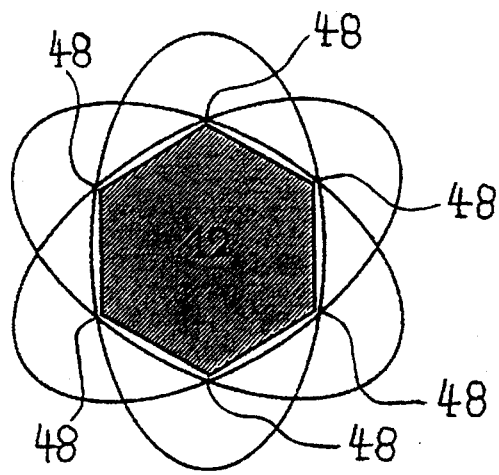
Figure 6C:
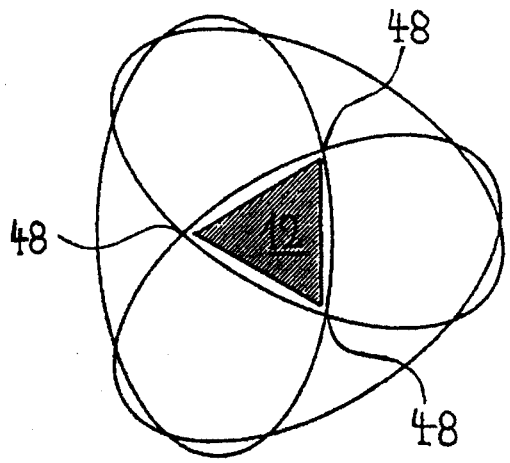

As in FIG. 6a, all the test coils in FIG. 6b have a common rotation axis. In the case of FIG. 6b three test coils of the same diameter are similarly tilted and rotated against one another about a common axis by 120° in each case parallel to the travel direction of the object 12. This makes it possible to cover an equal-sided, hexagonal object. Without changing the test coils and tilting state thereof, it is possible to produce a substantially triangular, common test cross-section, as shown in FIG. 6c. In this case the rotation axes of the individual coils no longer coincide and are instead staggered.

Figure 6D:
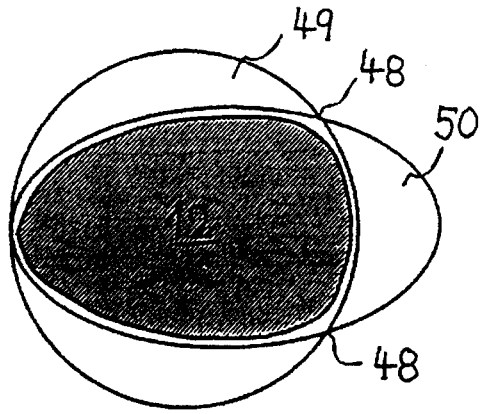

FIG. 6d shows how it is possible with an untilted test coil 49 and a tilted test coil 50, which has a larger diameter than the coil 49, to cover a test object 12 whose cross-section is substantially oval.

Figure 6E:
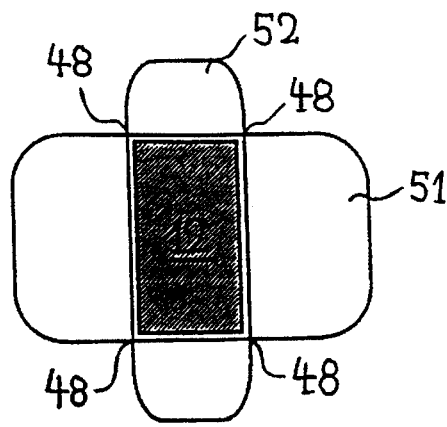

Finally, FIG. 6e shows two successively arranged test coils with partly linear segments. In the case of the untilted test coil 51 it can be seen that the test cross-section of such a coil is like a rectangle with rounded corners. The tilted test coil 52 turned by 90° about the travel direction against the test coil 51 has the same cross-section as the latter, but its test cross-section is modified by tilting. Both coils together cover the test object 12 with the rectangular cross-section.

I claim:

1. A method for electro-magnetically testing elongated test objects having cross sections of various shapes and comprising the steps of providing at least one test coil which defines a coil plane and which includes a coil plane passage of predetermined cross section, advancing an elongated test object along a travel direction and through the coil plane passage, and adjustably positioning the one test coil into a stationary position so that the coil plane passage may be adjusted with respect to the travel direction of the advancing elongated test object and so that when considered in the travel direction, the cross section of the coil passage closely conforms to at least a circumferential portion of the cross section of the elongated test object.

2. The method as defined in claim 1, wherein the coil plane passage has a circular cross section, wherein the elongated test object has an elliptical cross-section, and wherein the position of the test coil is selected so that when considered in the travel direction of the advancing elongated test object, the cross section of the coil plane passage is elliptical and generally conforms to the elliptical cross-section of the elongated test object.

3. The method as defined in claim 1, wherein the step of adjustably positioning the one test coil includes tilting the coil about an axis which lies in said coil plane and transverse to the travel direction of the elongated test object.

4. An apparatus for electro-magnetically testing elongated test objects having cross sections of various shapes and advancing in a travel direction, the apparatus comprising at least one test coil defining a coil plane and having a coil plane passage of predetermined cross section through which the test object is adapted to pass; and means operatively connected to the test coil for tilting the test coil into a stationary position about a tilt axis running traverse to the test object travel direction in such a way that, considered in the test object travel direction, the test coil has a test cross section differing from the coil plane passage cross section.

5. The testing apparatus according to claim 4, wherein the tilt axis runs perpendicular to the test object travel direction and parallel to the coil plane.

6. The testing apparatus according to claim 4, wherein the tilting means includes bearing means for supporting the test coil, the bearing means being arranged such that the test coil is rotatably mounted about the tilt axis on the bearing means.

7. The testing apparatus according to claim 6, wherein the bearing means is provided in the vicinity of a test coil circumference and wherein there are two bearing means on diametrically opposite sides of the test coil.

8. The testing apparatus according to claim 4, wherein the coil plane passage cross section is circular.

9. The testing apparatus according to claim 4, wherein the tilt axis passes centrally through the test coil.

10. The testing apparatus according to claim 6, further comprising at least one of the group consisting of a reception member, a rotary member, a sliding member, and wherein the bearing means engages one of said group.

11. The testing apparatus according to claim 6, further comprising bearing holding means for holding the bearing means, the bearing holding means being movably mounted on one of a group consisting of a reception member, a rotary member, and a sliding member.

12. The testing apparatus according to claim 6, wherein there is provided electrical line means electrically connected to the test coil for electrically connecting the test coil to means for electrical supply and evaluation.

13. The testing apparatus according to claim 4, further comprising a rotary member which is mounted for rotation about an axis which is parallel to the test object travel direction, and wherein the tilting means is mounted to said rotary member.

14. The testing apparatus according to claim 13, wherein there is defined a displacement plane perpendicular to the test object travel direction and wherein the rotary member is rotatably mounted on a sliding member which is displaceable in a direction parallel to the displacement plane.

15. The testing apparatus according to claim 4, wherein at least two of said test coils are successively arranged in the travel direction.

16. The testing apparatus according to claim 15, wherein said at least two test coils are connected in series.

17. The testing apparatus according to claim 15, wherein said at least two test coils are differentially connected to produce a differential signal.

18. The testing apparatus according to claim 15, wherein said at least two test coils form a coil group and wherein the tilt axes of the test coils of the coil group are parallel to one another and lie in a plane which is parallel to the travel direction.

19. The testing apparatus according to claim 15, further comprising tilt setting means engaging at least one test coil for tilting the at least one test coil, and including means for visibly displaying the setting of the tilt setting means.

20. The testing apparatus according to claim 18, wherein a plurality of said coil groups are successively arranged in the travel direction and are settable independently of one another.

21. The testing apparatus according to claim 4, wherein the one test coil is an eddy-current coil.

* * * * *

UNITED STATES PATENT AND TRADEMARK OFFICE
CERTIFICATE OF CORRECTION

PATENT NO. : 5,638,000
DATED : June 10, 1997
INVENTOR(S) : Friedrich M. Förster

It is certified that error appears in the above-identified patent and that said Letters Patent is hereby corrected as shown below:

Column 2, line 33, "she" should be -- the --.

Column 6, line 58, "FIG. 4" should be -- FIG. 1 --.

Column 8, line 1, delete "setscrew".

Signed and Sealed this

Twenty-fourth Day of February, 1998

Attest:

BRUCE LEHMAN

*Attesting Officer*      *Commissioner of Patents and Trademarks*